(12) United States Patent
Hamano et al.

(10) Patent No.: US 8,616,199 B2
(45) Date of Patent: Dec. 31, 2013

(54) INHALER AND EJECTION HEAD UNIT ATTACHABLE TO THE INHALER

(75) Inventors: Soji Hamano, Yokohama (JP); Mitsuru Imai, Chichibu (JP)

(73) Assignee: Canon Kabushiki Kaisha, Tokyo (JP)

( * ) Notice: Subject to any disclaimer, the term of this patent is extended or adjusted under 35 U.S.C. 154(b) by 964 days.

(21) Appl. No.: 12/036,610

(22) Filed: Feb. 25, 2008

(65) Prior Publication Data

US 2008/0223362 A1  Sep. 18, 2008

(30) Foreign Application Priority Data

Mar. 16, 2007  (JP) .................................. 2007-067973
Jan. 25, 2008  (JP) .................................. 2008-014431

(51) Int. Cl.
*A61M 15/00*  (2006.01)
*A61M 11/00*  (2006.01)

(52) U.S. Cl.
USPC ............ 128/203.12; 128/200.14; 128/200.16; 128/200.23

(58) Field of Classification Search
USPC ............ 128/200.14–200.23, 200.24, 203.12, 128/203.26, 203.27
See application file for complete search history.

(56) References Cited

U.S. PATENT DOCUMENTS

| 5,970,974 | A | * | 10/1999 | Van Der Linden et al. | 128/200.16 |
| 6,196,219 | B1 | * | 3/2001 | Hess et al. | 128/200.21 |
| 7,073,499 | B1 | | 7/2006 | Reinhold et al. | 128/200.18 |
| 2002/0134373 | A1 | * | 9/2002 | Gonda | 128/200.14 |
| 2004/0089299 | A1 | * | 5/2004 | Bonney et al. | 128/203.15 |
| 2004/0107961 | A1 | * | 6/2004 | Trueba | 128/200.16 |
| 2005/0172957 | A1 | * | 8/2005 | Childers et al. | 128/200.23 |
| 2006/0081239 | A1 | * | 4/2006 | Alley et al. | 128/200.14 |
| 2007/0062520 | A1 | | 3/2007 | Nobutani et al. | 128/200.14 |
| 2007/0227534 | A1 | | 10/2007 | Nobutani et al. | 128/200.14 |
| 2007/0240706 | A1 | | 10/2007 | Kobayashi et al. | 128/200.14 |
| 2007/0240711 | A1 | | 10/2007 | Hamano | 128/203.12 |
| 2008/0011292 | A1 | | 1/2008 | Sugita et al. | 128/200.19 |
| 2008/0022998 | A1 | | 1/2008 | Hamano et al. | 128/200.14 |
| 2008/0099011 | A1 | * | 5/2008 | Gonda et al. | 128/200.14 |

FOREIGN PATENT DOCUMENTS

| CA | 2037421 C | 9/1991 |
| DE | 4106379 A | 9/1991 |
| EP | 1317939 | 6/2003 |
| EP | 1475115 | 11/2004 |
| WO | 95/01137 | 1/1995 |
| WO | 02/04043 A2 | 1/2002 |

OTHER PUBLICATIONS

Office Action issued on Aug. 14, 2012 in counterpart Japanese Patent Application No. 2008-014431, with translation.

* cited by examiner

*Primary Examiner* — Justine Yu
*Assistant Examiner* — Valerie L Skorupa
(74) *Attorney, Agent, or Firm* — Fitzpatrick, Cella, Harper & Scinto (57) ABSTRACT

An ejection head unit is attachable to an inhaler for ejecting a medicine to cause a user to inhale the medicine and has a plurality of ejection heads having an element generating energy for ejecting the medicine, and a plurality of ejection nozzles through which the medicine is ejected by the element. An inhaler for ejecting a medicine to allow inhalation thereof by a user has an air flow path guiding a medicine that is inhaled accompanying inspiration by the user to a suction port, an ejection head unit having a plurality of ejection heads including an element generating energy for ejecting the medicine and a plurality of ejection nozzles through which the medicine is ejected by the element, and a positioning unit for positioning a single ejection head among the plurality of ejection heads at an opening provided in one portion of the air flow path.

14 Claims, 6 Drawing Sheets

INHALER AND EJECTION HEAD UNIT ATTACHABLE TO THE INHALER

BACKGROUND OF THE INVENTION

1. Field of the Invention

The present invention relates to an inhaler for ejecting a medicine to cause the medicine to be inhaled by a user. The present invention also relates to an ejection head unit that can be attached to the inhaler.

2. Description of the Related Art

In recent years, average life expectancy is increasing as a result of advances in the fields of medicine and science. This is leading to an increase in the elderly population. In particular, in so-called developed countries, an increase in patients with lifestyle-related diseases such as diabetes or hypertension has become a problem. On the other hand, the number of medical institutions is not increasing to a degree that can cope with the increase in these kinds of patients, and since there are some communities in which there are no medical institutions that such patients can attend, there is a concern about ways to cope with this problem in the future, including from the viewpoint of government policy.

A specific case will now be described. Among the diabetes patients that are increasing at present, patients suffering from insulin-dependent type diabetes, referred to as "type 1", need to be regularly administered doses of insulin, since they have no secretion of insulin from their pancreas. Because administration of insulin is currently performed by subcutaneous injection, the physical and mental burden on the patient is large.

A pen-type syringe with a thin needle that causes less pain to patients has been developed to lessen the burden on this kind of user. However, in most cases patients with type 1 diabetes lead a life that is similar to a person in normal health other than requiring regular administration of insulin. Therefore, since there is generally a mental resistance to administering an injection to oneself in front of other people, even with a pen-type syringe, it may be difficult for them to perform administration at an appropriate time. Consequently, there is a concern that appropriate treatment of the user will not be achieved out with this kind of method. Meanwhile, inhalers have been developed that allow a user to inhale minute droplets of a medicine solution by utilizing the ejection principles of an ink-jet system to eject the droplets into an air flow path in which air flows that is inhaled through a mouthpiece (see International Publication No. WO1995/01137 and International Publication No. WO2002/04043). This kind of inhaler has the advantage of enabling a predetermined amount of a medicine solution to be precisely sprayed in a uniform particle size.

The basic configuration of this kind of medicine-solution ejecting apparatus includes an ejection head in which an ejection energy generating element such as a heater element is disposed and a reservoir that stores a medicine solution that is supplied to the ejection head. For both a case in which the ejection head and the reservoir are integrated to include a cartridge and a case in which the ejection head and the reservoir are provided as separate members which are independently exchangeable, it is assumed that the same ejection head will be used for inhalation a plurality of times.

However, with an inhaler it is important that the particle size of a droplet is several microns, which is an extremely small size. Thus, it is necessary that the diameter of the ejection nozzle is also several microns. When performing inhalation a plurality of times with the same ejection head, residual medicine is liable to adhere to an inner wall of the ejection nozzle and block up the ejection nozzle. Consequently, there is the problem that the number of ejection orifices that eject droplets at the time of the next inhalation is reduced and the ejection amount is less than the predetermined ejection amount. Further, the interval inhalation may involve inhalation after each meal or inhalation once per day, and in that case a problem regarding a change in the properties of the medicine or regarding hygiene arises.

To solve such problems, although it is adequate to perform a suction and restoration operation utilizing a medicine solution in a similar manner to that employed in a known ink jet printer, it is not desirable to waste a high cost medicine solution, and the size of the apparatus also increases. As a result of these problems, it is necessary to perform the troublesome work of replacing the ejection head for each inhalation, and the actual situation is that the apparatus is impractical.

SUMMARY OF THE INVENTION

The present invention is directed to an inhaler that stabilizes an ejection amount to enable inhalation of an appropriate inhalation amount of medicine while reducing the labor of exchanging an ejection head for multiple inhalations.

One aspect of the present invention for overcoming the above problems is an ejection head unit attachable to an inhaler for ejecting a medicine to cause a user to inhale the medicine, including: a plurality of ejection heads that include an element that generates energy for ejecting the medicine and a plurality of ejection nozzles through which the medicine is ejected by the element.

Another aspect of the present invention for overcoming the above problems is an inhaler for ejecting a medicine to allow inhalation thereof by a user, including: an air flow path that guides a medicine to be inhaled accompanying inspiration by a user to a suction port; an ejection head unit including a plurality of ejection heads that include an element that generates energy for ejecting the medicine, and a plurality of ejection nozzles through which the medicine is ejected by the element; and positioning means for positioning a single ejection head among the plurality of ejection heads at an opening provided in one part of the air flow path.

The present invention as configured as described above provides the following effects.

Even when inhalation is performed a plurality of times with the same inhaler, a stabilized ejection amount of droplets of medicine from the ejection head can be maintained to enable a user to inhale a predetermined medicine amount. Further, the inconvenience caused by replacing an ejection head for each inhalation is reduced while maintaining hygienic inhalation conditions.

Other features and advantages of the present invention will be apparent from the following description taken in conjunction with the accompanying drawings, in which like reference characters designate the same or similar parts throughout the figures thereof.

DESCRIPTION OF THE EMBODIMENTS

Preferred embodiments of the present invention will now be described in detail according to the accompanying drawings.

Figure 1:
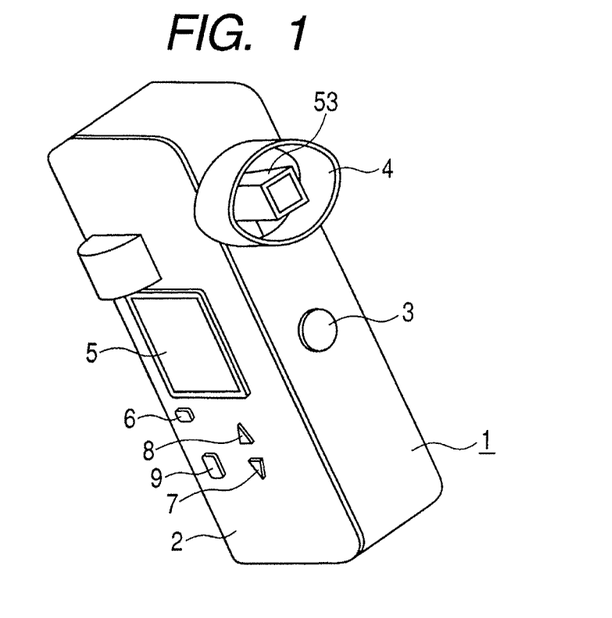
FIG. 1 is an exterior oblique perspective view that illustrates an inhaler according to a first embodiment of the present invention.

FIG. 1 is oblique perspective view in schematic form of an inhaler according to an embodiment of the present invention. In the inhaler according to the present embodiment, the main unit outer casing is formed with a box-shaped housing case 1 that has an open surface and an access cover 2. The access cover 2 is attached in a freely turnable state through a hinge (not shown) to one side edge of the open surface of the housing case 1, and is urged at all times to open by an unillustrated spring. A hook claw (not shown) is provided on an end (not shown) of the access cover 2 that is opposite the hinge. The hook claw can be locked by engaging the hook claw with an engaging portion that is integrated with a lock release button 3 when closing the access cover 2, so that the access cover 2 does not open accidentally. The configuration is such that, upon opening of the access cover 2, the hook claw is released from the engaging portion by pushing of the release button 3 so that the access cover 2 opens by the force of the spring. In addition, a display unit 5 for displaying the dosage, the time, and an error display is provided on the access cover 2. Further, a menu button 6 and an up button 8, a down button 7, and a decision button 9 as setting buttons are provided to allow the user to carry out settings.

Figure 2:
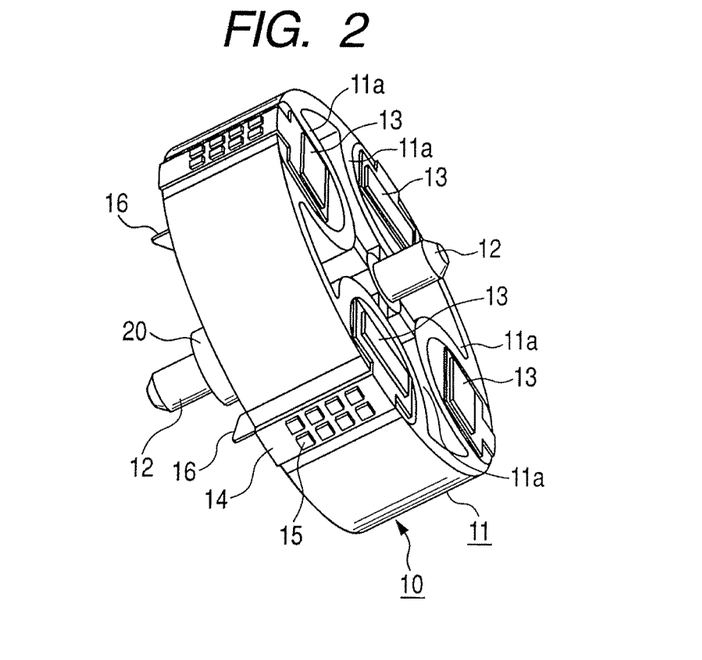
FIG. 2 is an exterior oblique perspective view of a revolver-type ejection head unit according to the first embodiment of the present invention.

The inhaler according to the present embodiment includes a revolver type ejection head unit. FIG. 2 is a schematic oblique perspective view of the revolver-type ejection head unit. As shown in FIG. 2, the ejection head unit 10 includes in a main body 11 a plurality of supporting portions 11a (four supporting portions are shown in the figure) that are disposed with intervals therebetween in the peripheral direction around a rotating shaft 12. In each of the supporting portions 11a, a respective ejection head 13 is detachably held and fixed. The ejection head unit is attachable to the inhaler.

The inhaler according to the present embodiment includes a revolver type ejection head unit. FIG. 2 is a schematic oblique perspective view of the revolver type ejection head unit. As shown in FIG. 2, the ejection head unit 10 includes in a main body 11a plurality of supporting portions 11a (four supporting portions are shown in the figure) that are disposed with intervals therebetween in the peripheral direction around a rotating shaft 12. In each of the supporting portions 11a, the respective ejection heads 13 are detachably held and fixed. The ejection head unit is attachable to the inhaler.

A plurality of ejection heads 13 are provided in the ejection head unit 10. Each ejection head 13 has a plurality of ejection nozzles for ejecting a medicine. An element that generates energy for ejecting the medicine is disposed in the vicinity of the ejection nozzles. As this element, a configuration having an electrothermal transducer that imparts thermal energy to a medicine (a so-called thermal ink-jet system) or an electromechanical transducer that imparts mechanical energy to the medicine (a so-called piezo ink-jet system) can be used. In particular, a thermal ink-jet system can be used. When using a thermal ink-jet system, the reproducibility and size precision with respect to the orifice diameter of the ejection nozzles, a thermal amount of a thermal pulse utilized for ejection, and a heater used therefor can be enhanced for each ejection head. Consequently, it is possible to achieve narrow droplet diameter distribution. Further, the production costs for the heads are low, and the applicability of the head to a small size apparatus for which it is necessary to frequently perform replacement is also high. Accordingly, in a case in which portability and convenience are required, such as the case of an inhaler, an ejection apparatus employing a thermal ink-jet system is particularly advantageous.

Figure 3:
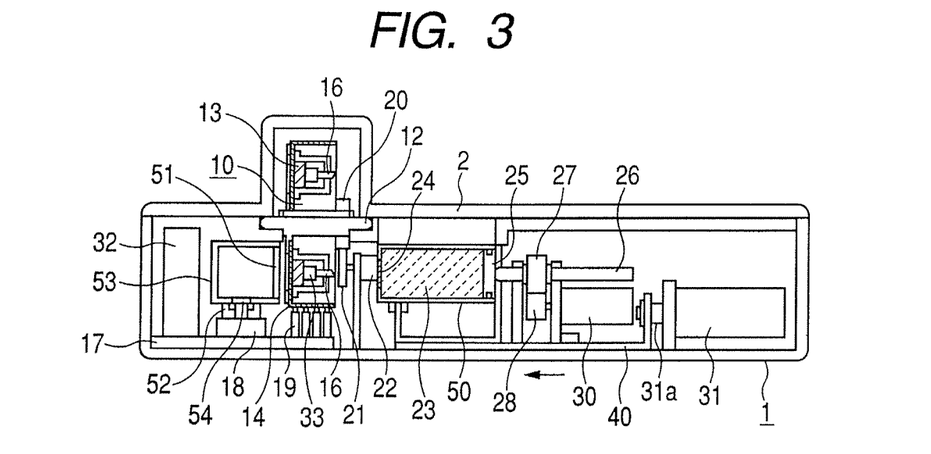
FIG. 3 is a schematic cross-sectional view of the inhaler before coupling an ejection head and a reservoir in the first embodiment.

FIG. 3 is a schematic cross-sectional view of an inhaler according to the present embodiment. As shown in FIG. 3, an opening 51 is provided in one portion of an air flow path 53 that is provided inside the housing case 1 and which guides medicine that the user inhale accompanying inspiration to a mouthpiece 4 (FIG. 1) as a suction port. Droplets of medicine that are ejected from the ejection head 13 that is positioned at an ejection position facing the opening 51 are introduced into an air flow of the air flow path 53. When the user inhales while using the mouthpiece 4, medicine is guided together with the inhaled air in the direction of the mouthpiece 4.

In order to synchronize inhalation of the user and ejection of droplets, the commencement of inhalation by the user is detected and the ejection of droplets is started based on an inhalation commencement detection signal. It is thereby possible to effectively perform inhalation of the medicine. For this purpose, a pressure sensor 18 as an inhalation detection sensor is provided in a control board 17. A pressure detection nozzle 52 of the pressure sensor 18 communicates with the air flow path 53 through a hole 54. That is, the configuration enables a negative pressure that is generated inside the air flow path 53 by inhalation by the user to be detected by the pressure sensor 18.

An inclination detection sensor (not shown) according to a 3-axis acceleration system is disposed in the control board 17. The inclination detection sensor is used to detect an abnormal inclination of the inhaler, and the detection result can be communicated to the user by being displayed on the display unit 5 provided on the access cover 2 accompanied by a sound or a vibration generated by a vibrating motor or illumination by an LED. Further, a RAM that stores prescription data or the like, a ROM that stores an operation program for the inhaler, and a CPU that controls the inhaler based on the data stored in the ROM and RAM are provided on the control board 17. A contact pin 19 for passing a current of a charging-type battery 32 to the ejection head 13 is provided on the control board 17. The contact pin 19 comes in contact with an electric contact point 15 on an electric contact member 14 that is adhered to the outer periphery of the ejection head unit 10. A communicating tube 16 for allowing the communication between the reservoir 50 that stores a medicine and the ejection head 13 is provided in correspondence with each ejection head 13 in the ejection head unit 10. However, the ejection head 13 and the reservoir 50 do not communicate prior to use. This is to prevent the medicine from undergoing a change in quality by contact with air, and is done in consideration of the safety of the medicine.

A flexible connecting membrane 24 is adherently disposed on the surface on the communicating tube 16 side of the reservoir 50, and prevents leakage of a medicine 23 from the reservoir 50.

Next, one ejection head among the plurality of ejection heads 13 is described with respect to positioning means for positioning the opening 51. The revolver type ejection head unit 10 is rotated by taking the rotating shaft 12 as the rotation center and the rotation is stopped at a position at which the ejection nozzle of an unused ejection head 13 matches with the opening 51 of the air flow path 53. To achieve this, a gear 20 is provided in an integrated condition with the rotating shaft 12 of the ejection head unit 10 so as to engage with a gear 21 that is mounted on a motor shaft of the ejection head driving motor 22. The ejection head unit 10 is rotated by a driving force of the ejection head driving motor 22, and a protrusion shape provided in the ejection head unit 10 is detected by a detection switch (a microswitch or a photosensor) to cause the ejection head unit 10 to stop at a position corresponding to the opening 51. More specifically, protrusions are provided in the ejection head unit 10 in the same amount as the amount of ejection heads 13, and are disposed so that their respective ejection heads 13 can be positioned at the opening 51 based on the relation with the detection switch. Positioning of the ejection head unit 10 may also be performed using an index plunger.

Next, adjustable means for causing the reservoir 50 to communicate with or separate from the ejection head 13 that is positioned at the opening is described.

Figure 4:
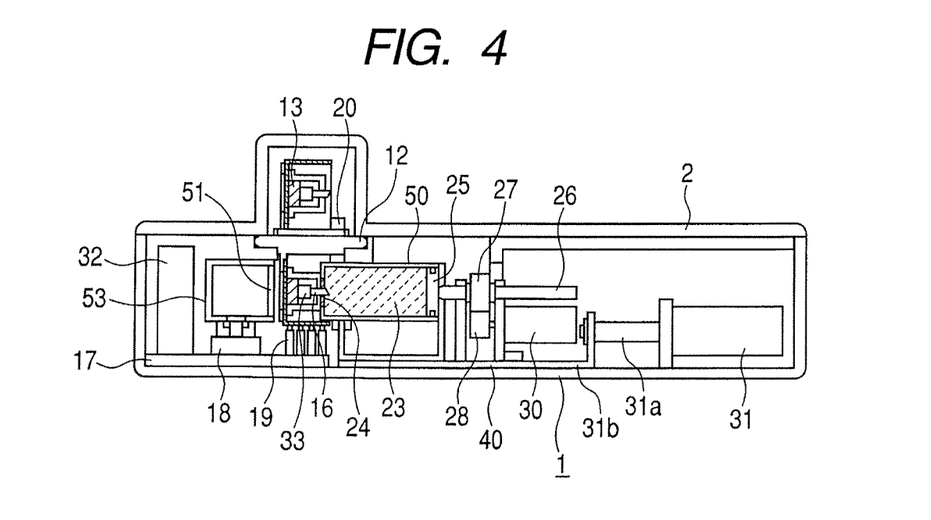
FIG. 4 is a schematic cross-sectional view of the inhaler after coupling the ejection head and the reservoir in the first embodiment.

The shape of a communicating tube 16 for filling medicine into a sub-reservoir 33 of the ejection head 13 has a pointed tip. By passing a current to a solenoid 31, bar 31b stretches and the reservoir 50 moves together with a movable carriage 40 to the ejection head 13 side, and the communicating tube 16 penetrates the connecting membrane 24 provided on the reservoir 50 so that the ejection head 13 and the reservoir 50 communicate. Since the purpose of the connecting membrane 24 is achieved as long as the connecting membrane 24 prevents a liquid leak and allows communication, the connecting membrane 24 may be a thick piece of rubber. In that case, by forming the communicating tube 16 using stainless steel and in a narrow shape like an injection needle, the communicating tube 16 can be inserted and extracted multiple times. This is an extremely effective connection method for a case in which the next inhalation is to be performed after an interval of a long time period, in which it is necessary to prevent contact between the medicine and air. FIG. 4 is a view illustrating a situation in which the solenoid 31 is operated to place the ejection head 13 and the reservoir 50 in a communicating state.

A motor 30 for filling the medicine into the ejection head 13 rotates a screw gear 27 through a gear 28. A screw thread shape is formed on the inner diameter side of the screw gear 27, and a screw shaft 26 is provided that meshes with the screw thread shape. A rotation stopping shape for changing a rotational motion into a linear motion is formed in the screw shaft 26. By pushing in a plunger (movable wall) 25 in the arrow direction shown in the figure, filling of medicine is performed that delivers the medicine 23 inside the reservoir 50 as far as the ejection head 13 via the communicating tube 16.

According to the present embodiment, a count area for the remaining number of unused ejection heads is provided in a storage portion (not shown: read and write enabled) inside the inhaler.

Figure 5:
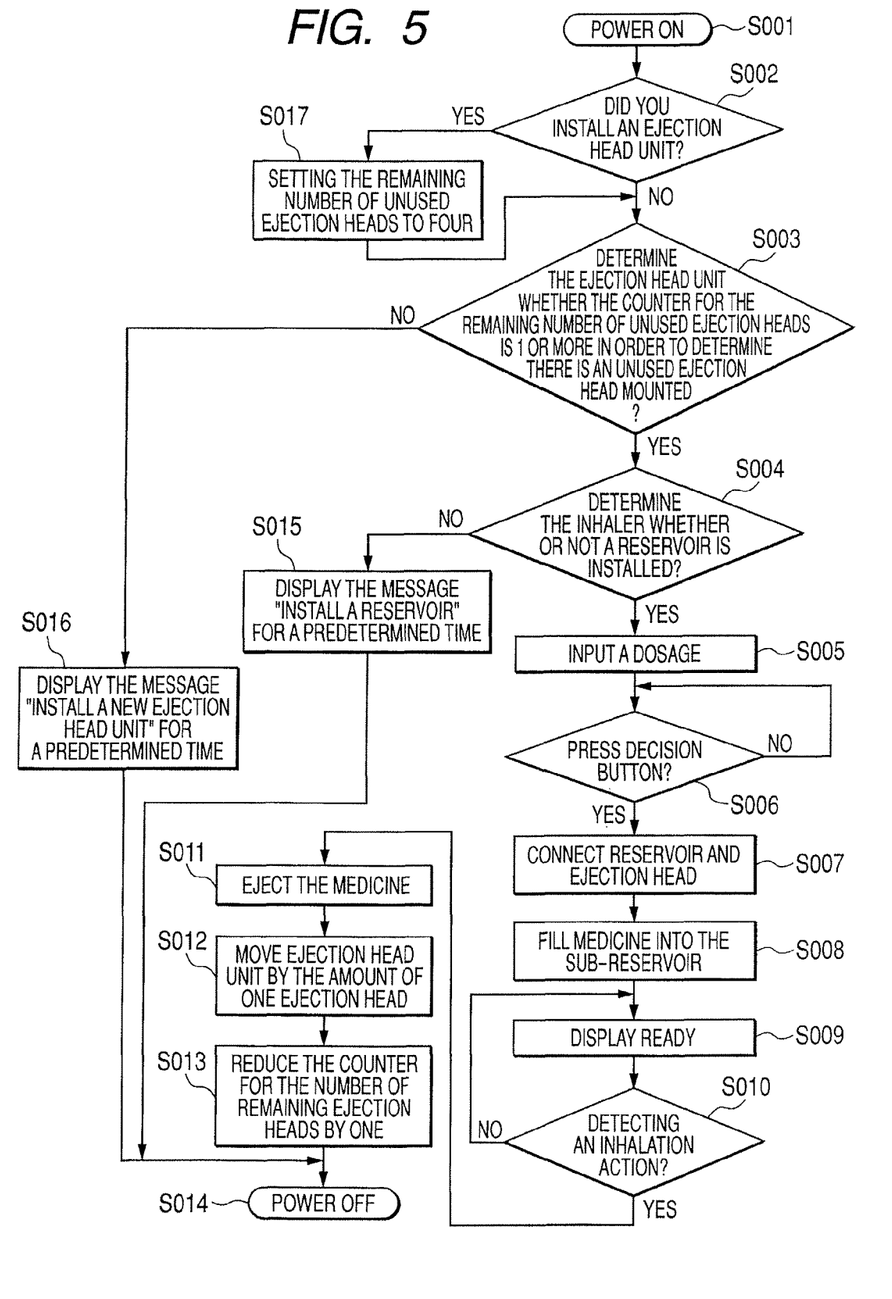
FIG. 5 is a flowchart of a first inhaler control example.

An example of the operations and actions of the present embodiment is now described according to the flowchart shown in FIG. 5.

The user sets the ejection head unit 10 that contains a plurality of the ejection heads 13 in the inhaler and also sets the reservoir 50 in the inhaler. Thereafter, when the user closes the access cover 2 of the inhaler, the inhaler executes initial settings such as displaying the message "Power On" on the display unit 5 (S001). Thereafter, at S002, the inhaler displays the message "Did you install an ejection head unit?" on the display unit 5, to request a decision from the user. If the user indicates "Yes" (presses the up setting button 8 of the inhaler), the inhaler switches to S017 to set the remaining number of unused ejection heads to four (initial value). Thereafter the inhaler switches to S003. If the user indicates "No" (presses the decision button directly), the inhaler switches to S003. At S003, the ejection head unit 10 determines whether the counter for the remaining number of unused ejection heads 13 is one or more in order to determine there is an unused ejection head 13 mounted. If the result is "No", the inhaler switches to S016 to display the message "Install a new ejection head unit" for a predetermined time, and then switches to S014. If the result at S003 is "Yes", the inhaler switches to S004. At S004, the inhaler determines whether or not a reservoir is installed. If the result is "No", the inhaler switches to S015. At S015, the message "Install a reservoir" is displayed for a predetermined time, and the inhaler then switches to S014. If the result at S004 is "Yes", the inhaler switches to a dosage input mode at S005. At this time, the inhaler displays the initial value "01" for medicine ejection on the display unit 5. The patient can cause the desired dosage amount to be displayed by operating the up setting button 8 and the down setting button 7 of the inhaler. Thereafter, the inhaler switches to S006 at which the user presses the decision button 9 to confirm the set dosage. The inhaler next switches to S007. At S007, the inhaler drives the solenoid 31 so as to move the reservoir 50 a predetermined distance, and pierces the connecting membrane 24 with the communicating tube 16 that protrudes from the sub-reservoir 33 to connect the sub-reservoir 33 and the reservoir 50. Thereafter, at S008, the inhaler rotates the motor 30 a predetermined amount to push the plunger 25 with the screw shaft 26 via the gear 28 and the screw gear 27 to thereby fill medicine into the sub-reservoir 33 and the ejection head 13. Next, at S009, the inhaler displays the message "Ready" (inhalation preparations complete) on the display unit 5, and at S010, waits for an inhalation action by the patient (detection of an inhalation action is performed by the pressure sensor 18). If the result of detection is "No" (negative pressure of an inhalation action is not detected), the inhaler continues to display "Ready" and to wait for an inhalation action. If the result of detection is "Yes" (negative pressure of an inhalation action is detected), the inhaler cancels the "Ready" display on the display unit 5 and proceeds to S011. At S011, the inhaler ejects a predetermined amount of medicine for a predetermined time. Thereafter, the inhaler switches to S012. At S012, the inhaler moves the ejection head unit by "the amount of one ejection head" (stops an unused ejection head at a position facing the opening 51). Next, the inhaler switches to S013 to reduce the counter for the number of remaining ejection heads 13 by one. The inhaler then switches to S014, at which the inhaler cancels the "Power On" message that is displayed on the display unit 5 and switches to a "power off" mode. Thereafter, the inhaler waits to switch to S001 (Power On) when the access cover 2 of the inhaler is closed by the user.

Figure 6:
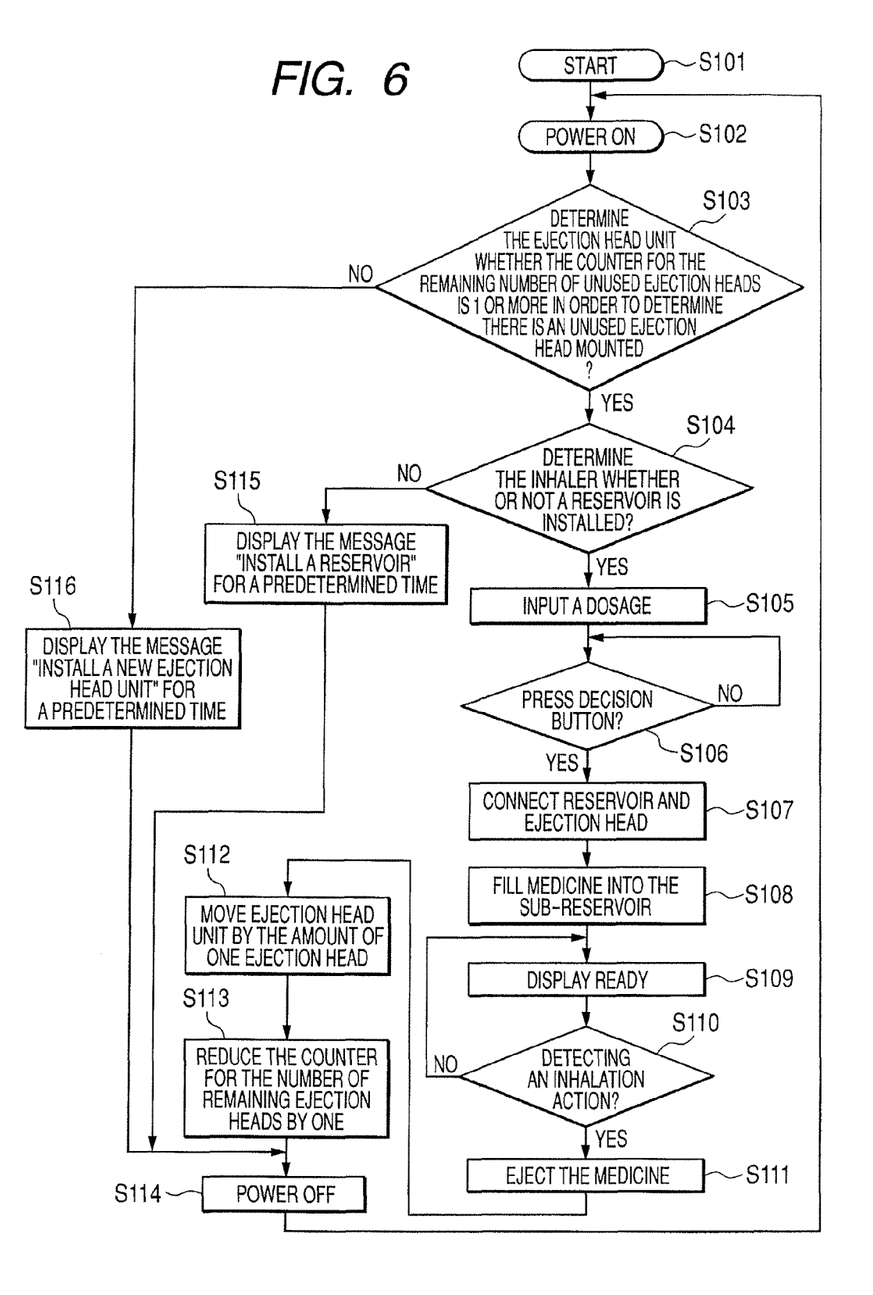
FIG. 6 is a flowchart of a second inhaler control example.

FIG. 6 is a flowchart that illustrates operations of a modification example that stores a counter value for the remaining number of unused ejection heads 13 inside the ejection head unit 10.

According to the present modification example, a counter value "4" for the remaining number of unused ejection heads 13 is written in a storage portion (not shown: read and write enabled) inside the ejection head unit 10 at the time of factory shipment.

The patient sets the ejection head unit 10 that contains a plurality of the ejection heads 13 in the inhaler and also sets the reservoir 50 in the inhaler. Thereafter, when the user closes the access cover 2 of the inhaler, the inhaler displays the message "Power On" on the display unit 5 (S102). The inhaler then electrically determines through the contact pin 19 that the ejection head unit 10 is installed and whether or not there are any unused ejection heads (S103). That is, the inhaler reads out the counter value for the remaining number of unused ejection heads 13 from the storage portion (not shown) of the ejection head unit 10 via the contact pin 19, and determines whether the counter for the remaining number of unused ejection heads 13 is one or more. If the result is "No", the inhaler switches to S116 to display the message "Install a new ejection head unit" for a predetermined time, and then switches to S114. If the result at S103 is "Yes", the inhaler switches to S104. At S104, the inhaler determines whether or not a reservoir is installed. If the result is "No", the inhaler switches to S115. At S115, the inhaler displays the message "Install a reservoir" for a predetermined time, and then switches to S114. If the result at S104 is "Yes", the inhaler switches to a dosage input mode at S105. At this time, the inhaler displays the initial value "01" for medicine ejection on the display unit 5. The patient can cause the desired dosage amount to be displayed by operating the up setting button 8 and the down setting button 7 of the inhaler. Thereafter, the inhaler switches to S106 at which the user presses the decision button 9 to confirm the set dosage. The inhaler then switches to S107. At S107, the inhaler drives the solenoid 31 so as to move the reservoir 50 a predetermined distance, and pierces the connecting membrane 24 with the communicating tube 16 that protrudes from the sub-reservoir 33 to connect the sub-reservoir 33 and the reservoir 50. Thereafter, at S108, the inhaler rotates the motor 30 a predetermined amount to push the plunger with the screw shaft 26 via the gear 28 and the screw gear 27 to thereby fill medicine into the sub-reservoir 33 and the ejection head 13. Next, at S109, the inhaler displays the message "Ready" (inhalation preparations complete) on the display unit 5, and at S110, waits for an inhalation action by the patient (detection of an inhalation action is performed by the pressure sensor 18). If the result of detection is "No", the inhaler continues to display "Ready" and wait for an inhalation action. If the result of detection is "Yes", the inhaler cancels the "Ready" display on the display unit 5 and proceeds to S111. At S111, the inhaler ejects a predetermined amount of medicine for a predetermined time. Thereafter, the inhaler switches to S112. At S112, the inhaler moves the ejection head 13 by "the amount of one ejection head" (stops an unused ejection head at a position facing the opening 51). Next, the inhaler switches to S113. At S113, the inhaler reads out the count value for the remaining number of unused ejection heads that is stored in the ejection head unit 10 through the contact pin 19, and writes in a new value in which the value that was read out is reduced by one. Thereafter, the inhaler switches to S114 to cancel the "Power On" message that is displayed on the display unit 5, switches to a "power off" mode, and returns to S102.

Figure 7:
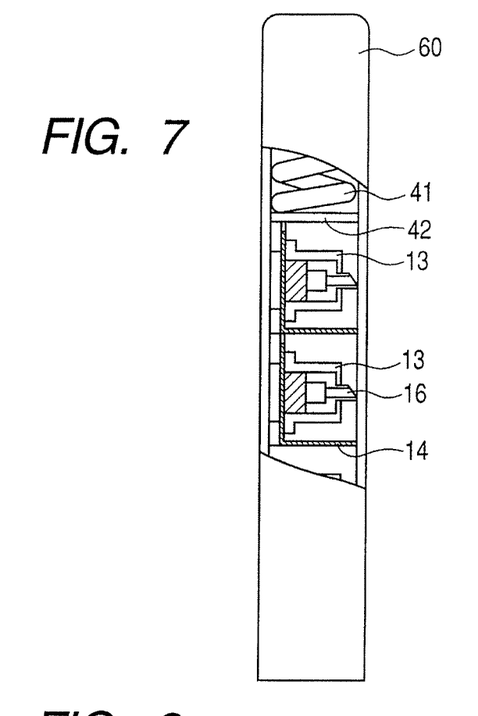
FIG. 7 is an external view of an ejection head unit according to a second embodiment of the present invention.

Next, an inhaler and an ejection head unit according to a second embodiment of the present invention are described while referring to FIG. 7 to FIG. 10. FIG. 7 is a schematic external view of the ejection head unit according to the present embodiment. The ejection head unit of the present embodiment has a housing for accommodating a plurality of ejection heads within the ejection head unit. According to the present embodiment, a plurality of ejection heads 13 is stored in a row inside a housing 60 in an overlapping state. By mounting the housing 60 in the inhaler, a plurality of ejection heads can be mounted with one operation.

Figure 8:
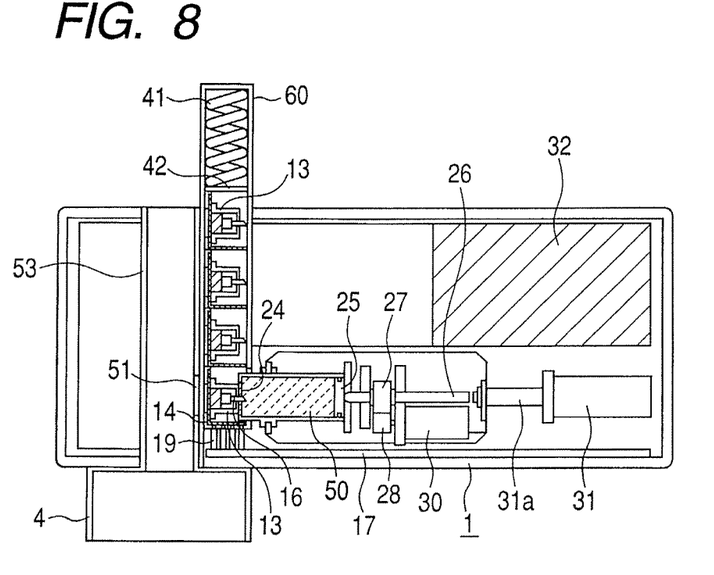
FIG. 8 is a schematic cross-sectional view of an inhaler after coupling an ejection head and a reservoir in the second embodiment.

As shown in FIG. 8, inside the housing 60 is contained a compression spring 41 for moving the ejection head 13, and an ejection head 13 is pressurized at all times through a pressure plate 42 in the direction of the opposite face of the compression spring 41. As a result, an ejection head 13 at the end opposite the pressure plate is positioned at an ejection position facing the opening 51. Thereafter, by passing a current to the solenoid 31, the reservoir 50 that stores medicine corresponding to an inhalation amount for a plurality of times moves in a direction such that the connecting membrane 24 is pierced by the communicating tube 16 of the ejection head 13, to enter a communicating state with respect to the ejection head 13. Further, the gear 28 rotates as a result of rotation of the motor 30, to thereby rotate the screw gear 27 that is engaged with the gear 28. Thereupon, the medicine filling screw shaft 26 that is disposed so as to mesh with the screw thread shape on the inner diameter side of the screw gear 27 pushes in the medicine filling plunger 25. Thus, filling of medicine in which medicine passes through the communicating tube 16 to the ejection head 13 is performed.

A contact pin 19 for passing a current of a charging-type battery 32 to the ejection head 13 is provided on the control board 17. The contact pin 19 comes in contact with an electric contact point 15 on an electric contact member 14 that is adhered to the outer periphery of the ejection head 13.

Figure 9:
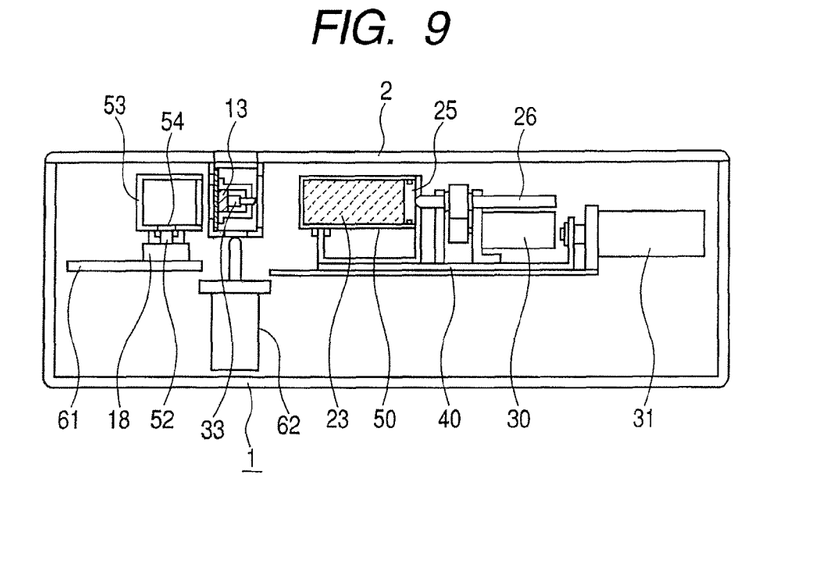
FIG. 9 is a schematic cross-sectional view of the inhaler before coupling the ejection head and the reservoir in the second embodiment.

FIG. 9 is a cross-sectional view that illustrates a state in which filling of medicine to the sub-reservoir 33 and the ejection head 13 is complete, the passage of current to the solenoid 31 is turned off, and the reservoir 50 has returned to a standby state. In this state the inhaler waits for inhalation by the user. When inhalation by the user is detected, the inhaler commences ejection based on an inhalation detection signal. The pressure sensor 18 is provided on a sensor board 61 as an inhalation detection sensor. A hole 54 is provided in a part of the air flow path 53 that corresponds to the pressure detection nozzle 52 of the pressure sensor 18.

Figure 10:
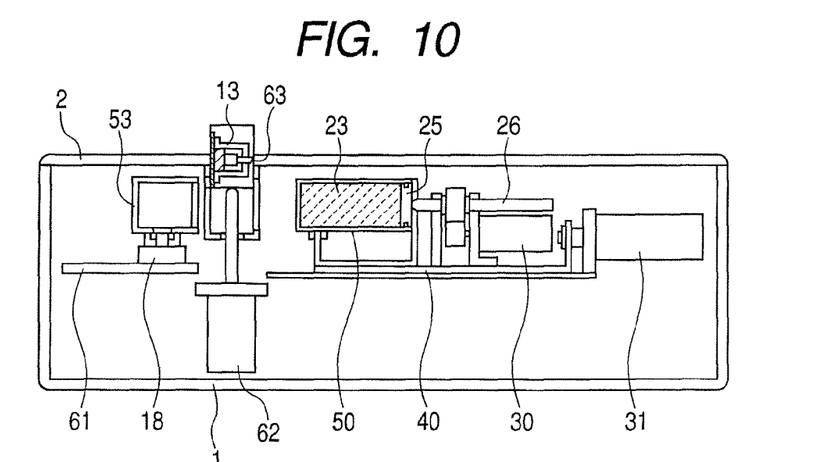
FIG. 10 is a schematic cross-sectional view illustrating a state in which a spent ejection head is taken out with respect to the inhaler of the second embodiment.

FIG. 10 is a cross-sectional view illustrating a state in which an ejection head 13 is taken out. When replacing an ejection head 13, the inhaler activates a solenoid 62 for discharging an ejection head to push out the used ejection head that is at an ejectable position to outside of the inhaler from an ejection head outlet 63 that is provided in the access cover 2. An outlet is also provided at one part of the housing 60 of the ejection head unit so as to match the position of the outlet 63. When pushing of the ejection head to outside is completed, the inhaler turns off the passage of current to the solenoid and returns to a standby position. An unused ejection head that was adjacent to the ejection head that is removed in the housing 60 is slidingly moved by the force of the compression spring 41 shown in FIG. 7 to a position in which ejection is enabled in the space from which the ejection head was pushed out. More specifically, the compression spring 41 fulfills a function as a pushing mechanism that, when the ejection head is removed from the outlet 63, slides the next ejection head to the position at which ejection is possible, and a function as positioning means for positioning a single ejection head among the plurality of ejection heads at the opening 51. At the next inhalation, medicine is filled again into the unused ejection head and inhalation performed. When there are no more unused ejection heads, the housing 60 is replaced. The operation flowchart is the same as in the first embodiment, and is thus omitted here. In this connection, in the inhaler according to the present embodiment it is not necessary that the ejection head unit includes the housing 60. The configuration may be one in which a plurality of ejection heads are unitized and stored in one row inside the inhaler.

The inhaler of the present invention is not limited to use for inhaling medicine and can be used for various uses that require certain and hygienic droplet ejection. For example, the inhaler of the present invention can also be used for a mist ejection apparatus for ejecting an aromatic substance or for an inhaler of a substance of liking of a user such as nicotine.

The present invention is not limited to the above embodiments and various changes and modifications can be made within the spirit and scope of the present invention. Therefore to apprise the public of the scope of the present invention, the following claims are made.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2007-067973, filed Mar. 16, 2007, and No. 2008-014431, filed Jan. 25, 2008, which are hereby incorporated by reference herein in their entirety.

What is claimed is:

1. An inhaler for ejecting a medicine to allow inhalation thereof by a user, comprising:
   an air flow path that guides a medicine that is inhaled to a suction port accompanying inspiration by the user;
   an ejection head unit attachable to an inhaler main unit and comprising a plurality of ejection heads that include an element that generates energy for ejecting the medicine, and include a plurality of ejection nozzles through which the medicine is ejected by said element;
   a reservoir for storing the medicine, said reservoir being a separate unit from the inhaler main unit and being attachable to the inhaler main unit, wherein said ejection head unit is detachable from the inhaler main unit and can be detached from the inhaler main unit without detaching said reservoir from the inhaler main unit;
   a moving means for returning said reservoir to a standby position in which said reservoir is separate from said ejection head unit to take said reservoir and said single ejection head out of communication with each other after said reservoir is moved toward said single ejection head to communicate with said ejection head; and
   positioning means for positioning a single ejection head among said plurality of ejection heads at an opening provided in one portion of said air flow path,
   wherein the ejection head ejects a medicine in a state in which said reservoir is positioned in said standby position.

2. The inhaler according to claim 1, further comprising a plurality of supporting portions that fix said plurality of ejection heads, wherein said supporting portions are provided so that said ejection heads are disposed at intervals with respect to each other in a peripheral direction around a rotating shaft.

3. The inhaler according to claim 1, further comprising:
   a housing that houses said plurality of ejection heads on the inside thereof, said housing having an outlet in one portion of said housing for removing a used ejection head at a position at which ejection is enabled; and
   a pushing mechanism that, when an ejection head is removed from said outlet, slides an ejection head that was adjacent inside the housing to the ejection head that is removed, to the position at which ejection is enabled.

4. The inhaler according to claim 1, further comprising:
   adjustable means for causing said reservoir to communicate with or separate from said single ejection head that is positioned at said opening.

5. The inhaler according to claim 1, wherein
   said ejection head unit includes a plurality of supporting portions that are provided at intervals with respect to each other in a peripheral direction around a rotating shaft, and respective ones of said ejection heads are retained on respective ones of said supporting portions, and
   said positioning means positions an unused ejection head at said opening by rotating in a manner that takes the rotating shaft as a center of rotation.

6. The inhaler according to claim 1, wherein, in said ejection head unit, a plurality of said ejection heads are disposed in a row, and when a used ejection head is removed, an unused ejection head is positioned at said opening.

7. The inhaler according to claim 1, wherein said element includes an electrothermal transducer that imparts thermal energy to the medicine or an electromechanical transducer that imparts mechanical energy to the medicine.

8. An inhaler for ejecting a medicine to allow inhalation thereof by a user, comprising:
   an air flow path that guides a medicine that is inhaled to a suction port accompanying inspiration by the user;
   an ejection head unit attachable to an inhaler main unit and comprising a plurality of ejection heads that include an element that generates energy for ejecting the medicine, and include a plurality of ejection nozzles through which the medicine is ejected by said element, each of said ejection heads having an inlet portion for supply of the medicine into said ejection head, and said ejection head unit being movable in a first direction to move successive ones of said ejection heads to an opening provided in one portion of said air flow path;
   positioning means for moving said ejection head unit in said first direction to position a single ejection head among said plurality of ejection heads at said opening;
   a reservoir for storing the medicine, said reservoir being a separate unit from the inhaler main unit and being attachable to the inhaler main unit, said reservoir having an outlet portion for supplying the medicine to one of said ejection heads of said ejection head unit when said reservoir is in a first position; and
   a moving means for moving said reservoir into said first position and thereby moving said outlet portion into communication with said one of said single ejection heads, and for subsequently returning said reservoir from said first position to a standby position in which said reservoir is spaced from said ejection head unit to take said reservoir and said one ejection head out of communication with each other, said moving means moving in a second direction different from said first direction to move said reservoir from said first position into said standby position, wherein said single ejection head ejects a medicine in a state in which said reservoir is positioned in said standby position.

9. The inhaler according to claim 8, further comprising a plurality of supporting portions that fix said plurality of ejection heads, wherein said supporting portions are provided so that said ejection heads are disposed at intervals with respect to each other in a peripheral direction around a rotating shaft.

10. The inhaler according to claim 8, further comprising:
a housing that houses said plurality of ejection heads on the inside thereof, said housing having an outlet in one portion of said housing for removing a used ejection head at a position at which ejection is enabled; and
a pushing mechanism that, when an ejection head is removed from said outlet, slides an ejection head that was adjacent inside the housing to the ejection head that is removed, to the position at which ejection is enabled.

11. The inhaler according to claim 8, further comprising:
adjustable means for causing said reservoir to communicate with or separate from said single ejection head that is positioned at said opening.

12. The inhaler according to claim 8, wherein
said ejection head unit includes a plurality of supporting portions that are provided at intervals with respect to each other in a peripheral direction around a rotating shaft, and respective ones of said ejection heads are retained on respective ones of said supporting portions, and said positioning means positions an unused ejection head at said opening by rotating in a manner that takes the rotating shaft as a center of rotation.

13. The inhaler according to claim 8, wherein, in said ejection head unit, a plurality of said ejection heads are disposed in a row, and when a used ejection head is removed, an unused ejection head is positioned at said opening.

14. The inhaler according to claim 8, wherein said element includes an electrothermal transducer that imparts thermal energy to the medicine or an electromechanical transducer that imparts mechanical energy to the medicine.

* * * * *